United States Patent
Lalgudi et al.

(10) Patent No.: US 10,669,225 B2
(45) Date of Patent: Jun. 2, 2020

(54) METHODS OF MAKING 1,19-NONADECANEDIESTER AND DERIVATIVES THEREOF

(71) Applicant: Battelle Memorial Institute, Columbus, OH (US)

(72) Inventors: Ramanathan S. Lalgudi, Westerville, OH (US); Jeffrey Cafmeyer, Columbus, OH (US); Robert J. Cain, Lewis Center, OH (US); Daniel Garbark, Blacklick, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 15/775,642

(22) PCT Filed: Nov. 9, 2016

(86) PCT No.: PCT/US2016/061116
§ 371 (c)(1),
(2) Date: May 11, 2018

(87) PCT Pub. No.: WO2017/083372
PCT Pub. Date: May 18, 2017

(65) Prior Publication Data
US 2018/0370897 A1 Dec. 27, 2018

Related U.S. Application Data

(60) Provisional application No. 62/253,986, filed on Nov. 11, 2015.

(51) Int. Cl.
| | |
|---|---|
| *C07C 67/38* | (2006.01) |
| *C07C 67/03* | (2006.01) |
| *C07C 51/41* | (2006.01) |
| *C08G 63/16* | (2006.01) |
| *C08G 69/26* | (2006.01) |
| *C07D 235/20* | (2006.01) |

(52) U.S. Cl.
CPC ............ *C07C 67/38* (2013.01); *C07C 51/412* (2013.01); *C07C 67/03* (2013.01); *C07D 235/20* (2013.01); *C08G 63/16* (2013.01); *C08G 69/26* (2013.01)

(58) Field of Classification Search
CPC ........ C07C 67/38; C07C 51/412; C07C 67/03
See application file for complete search history.

(56) References Cited

U.S. PATENT DOCUMENTS

| | | | |
|---|---|---|---|
| 2,966,478 A | 12/1960 | Harrison | |
| 3,937,687 A | 2/1976 | Rogier et al. | |
| 4,247,569 A | 1/1981 | Hata et al. | |
| 4,673,727 A | 6/1987 | Miller, Jr. | |
| 8,604,227 B2 | 12/2013 | Petrat et al. | |
| 2013/0030075 A1 | 1/2013 | Mecking et al. | |
| 2015/0315117 A1* | 11/2015 | Beuhler | C07C 67/03 |
| | | | 560/180 |

FOREIGN PATENT DOCUMENTS

| | | | |
|---|---|---|---|
| BE | 631293 | 4/1963 | |
| DE | 1074856 | 2/1960 | |
| DE | 1520908 A | 7/1969 | |
| DE | 1593575 A | 10/1969 | |
| DE | 1594634 A | 10/1970 | |
| DE | 1745464 A1 | 9/1971 | |
| DE | 3325156 | 1/1984 | |
| EP | 2774951 A1 * | 9/2014 | B32B 27/36 |
| EP | 2774951 A1 | 9/2014 | |

OTHER PUBLICATIONS

Kreuchunas, Journal of the American Chemical Society, The Synthesis of Higher Aliphatic , a, w-Dicarboxylic Acids, 1952, 75, pp. 3339-3344. (Year: 1952).*
Florian Stempfle, et al., Long-Chain Linear C 19 and C 23 Monomers and Polycondensates from Unsaturated Fatty Acid Esters, Macromolecules, vol. 44, No. 11, 4159-4166, Jun. 2011.
International Search Report and Written Opinion for application No. PCT/US2016/061116, dated Apr. 6, 2017.
Buu-Hoi, N.P., et al., Synthesis of Higher Aliphatic Diacids by Hydrogenolysis of Thiophene Derivatives, Bull. Soc. Chim. Fr., 1583-1586, 1955 (Abstract only).
Furst, Marc R.L., et al., Polymer Precursors from Catalytic Reactions of Natural Oils, Green Chemistry, 14 (2012), 2-s. 472-477.
Ortmann, Patrick, et al., Physical Properties and Hydrolytic Degradability of Polyethylene-like Polyacetals and Polycarbonates, Green Chemistry, 2014, 16, 1816-1827.

* cited by examiner

*Primary Examiner* — Paul A Zucker
(74) *Attorney, Agent, or Firm* — Green, Burns & Crain Ltd.

(57) ABSTRACT

Linear α, ω-nonadecanediester derivatives and methods of making the derivatives are described. The methods include reacting a linear α, ω-nonadecanediester or a linear α, ω-nonadecanedicarboxylic acid with a reactant optionally in the presence of at least one of a solvent and a catalyst to form the α, ω-nonadecanediester derivative. Methods of making linear α, ω-nonadecanediester or diester derivatives are also described.

15 Claims, No Drawings

METHODS OF MAKING 1,19-NONADECANEDIESTER AND DERIVATIVES THEREOF

This application is U.S. National Phase under 35 U.S.C. § 371 of International Application No. PCT/US2016/061116, entitled Methods of Making 1, 19-Nonadecanediesters And Derivatives Thereof, filed Nov. 9, 2016, which claims the benefit of U.S. Application Ser. No. 62/253,986, entitled Methods of Making $C_{19}$ Dicarboxylic Acids And Derivatives Thereof, filed Nov. 11, 2015, each of which is incorporated herein by reference in its entirety.

BACKGROUND OF THE INVENTION

Linear $\alpha$, $\omega$-long chain dialkyl esters are known in the art. They are used in industrial chemical processes, such as the production of polyesters and polyamides.

They have been made by reacting carbon monoxide with purified unsaturated fatty acids or their corresponding alkyl esters. They have also been made directly from high oleic soybean oil or the corresponding triglycerides, as described in U.S. Pat. No. 8,604,227.

However, these processes utilized methanesulfonic acid, which must be neutralized. It would be desirable to have a process which did not require neutralization of the methanesulfonic acid.

Derivatives of $\alpha$, $\omega$-long chain dialkyl esters, such as diols and diamides, are also known. However, it would be desirable to have additional derivatives.

Therefore, there is a need for an improved process of making $\alpha$, $\omega$-long chain dialkyl esters. There is also a need for new and useful derivatives of $\alpha$, $\omega$-long chain dialkyl esters, and for methods of making such derivatives.

SUMMARY OF THE INVENTION

One aspect of the invention is a method of making a linear $\alpha$, $\omega$-nonadecanediester derivative. In one embodiment, the method includes reacting a linear $\alpha$, $\omega$-nonadecanediester or a linear $\alpha$, $\omega$-nonadecanedicarboxylic acid with a reactant optionally in the presence of at least one of a solvent and a catalyst to form the $\alpha$, $\omega$-nonadecanediester nonadecanediester derivative; wherein the reactant is a metallic base or an ammonium base and the $\alpha$, $\omega$-nonadecanediester derivative is an $\alpha$, $\omega$-nonadecane di-metal salt; or wherein the reactant is a poly alkoxy diol, and the $\alpha$, $\omega$-nonadecanediester derivative is an $\alpha$, $\omega$-nonadecane di-poly alkoxy diol; or wherein the reactant is a caprolactone polyol and the $\alpha$, $\omega$-nonadecanediester derivative is an $\alpha$, $\omega$-nonadecane di-poly oxepan-2-one; or wherein the reactant is benzimidizole, and wherein the $\alpha$, $\omega$-nonadecanediester derivative is an $\alpha$, $\omega$-nonadecane di-benzimidizole; or wherein the reactant is an amine selected from piperazine, 1,4-diamino cyclohexane, isophorone diamine, and dicyclohexyl methane diamine, and wherein the $\alpha$, $\omega$-nonadecanediester derivative is an $\alpha$, $\omega$-nonadecane alt-(amine), wherein the alt-(amine) is derived from piperazine, 1,4-diamino cyclohexane, isophorone diamine, and dicyclohexyl methane diamine.

Another aspect of the invention involves $\alpha$, $\omega$-nonadecanediester derivatives. In one embodiment, the $\alpha$, $\omega$-nonadecanediester derivatives include an $\alpha$, $\omega$-nonadecane di-metal salt, an $\alpha$, $\omega$-nonadecane di-poly alkoxy diol, an $\alpha$, $\omega$-nonadecane di-poly oxepan-2-one, an $\alpha$, $\omega$-nonadecane di-benzimidizole, or an $\alpha$, $\omega$-nonadecane alt-(amine) wherein the alt-(amine) is derived from piperazine, 1,4-diamino cyclohexane, isophorone diamine, and dicyclohexyl methane diamine.

Another aspect of the invention is method of making a linear $\alpha$, $\omega$-nonadecanediester or diester derivative. In some embodiments, the method includes contacting a feed comprising a vegetable oil, a free fatty acid alkyl ester mixture, or an animal fat wherein at least about 50% of the fatty acid radicals or free fatty acid groups are oleic acid with an alcohol in the presence of carbon monoxide, a catalyst comprising a Group VIIIB element and a phosphorus containing ligand, and a solid silica support acid in a reactor to form a reaction mixture comprising the $\alpha$, $\omega$-nonadecanediester, the catalyst, and the solid support acid; crystallizing the $\alpha$, $\omega$-nonadecanediester; filtering the crystallized $\alpha$, $\omega$-nonadecanediester from the reaction mixture to form a filtrate; dissolving the crystallized $\alpha$, $\omega$-nonadecanediester in a first solvent to form a first solution; filtering the Group VIIIB element and the solid silica support acid from the first solution; and removing the first solvent from the first solution to provide a recrystallized $\alpha$, $\omega$-nonadecanediester.

DETAILED DESCRIPTION OF THE INVENTION

One aspect of the invention is a chemical process for the production of saturated $C_{19}$ diesters from triglycerides or free fatty acid alkyl esters. The process demonstrates the applicability for the formation and purification of polymer grade $C_{19}$ diesters from both soybean oil and the alkyl esters of soybean oil. The $C_{19}$ diester can be reacted with hexamethylenediamine in the production of a polyamide polymer.

The saturated $C_{19}$ dimethyl ester exhibits preferred crystallization behavior which allows it to be isolated in high yields and purity with a minimum number of steps. The $C_{19}$ dimethyl ester product can be used directly to produce polyesters or polyamides via transesterification or amidification reactions or it could be hydrolyzed to the dibasic acid, if desired. It can also be reacted with a variety of reactants to produce novel derivations of the $C_{19}$ dimethyl ester.

The feedstock can be vegetable oils, mixtures of fatty acid alkyl esters, or an animal fat. In some embodiments, the feedstock has at least about 50 wt % of the free fatty acid groups being oleic acid, or at least about 60 wt %, or at least about 70 wt %. It is advantageous to use feeds containing higher levels of oleic acid because the purification process is simplified. Suitable feedstock includes, but is not limited to, normal soybean oil, mid oleic soybean oil, high oleic soybean oil, high oleic canola oil, high oleic safflower oil, high oleic sunflower oil, high oleic olive oil, carinata oil, or combinations thereof. Regular soybean oil has about 20-25 wt % oleic acid, mid oleic soybean oil has an oleic content between the two, such as about 50 wt % to about 70 wt % oleic acid, and high oleic soybean oil has about 70 wt % or more oleic acid. The feedstock could also be vegetable oils having high levels of erucic acid, e.g., at least about 25 wt %, or about 25-40% erucic acid. Suitable feedstocks with high erucic acid include, but are not limited to, rapeseed oil and mustard oil. Alkyl esters of the vegetable oils and animal fats could also be used. Mixtures of fatty acid alkyl esters, such as biodiesel, could also be used. Alkyl esters include, but are not limited to, methyl esters, ethyl esters, propyl esters, isopropyl esters, butyl esters, isobutyl esters, 2-ethyl hexyl esters, amyl esters.

The feed is reacted with an alcohol. Suitable alcohols include, but are not limited to alcohols having 1 to 6 carbon atoms. One example of a suitable alcohol is methanol.

The process utilizes a methoxycarboxylation catalyst. The catalyst includes an element from Group VIIIB of the Periodic Table and a ligand.

Suitable elements from Group VIIIB include, but are not limited to, palladium.

Suitable ligands include phosphorus containing ligands. Suitable phosphorus containing ligands include, but are not limited to, phosphines, phosphinites, and phosphonites. Examples of suitable ligands include, but are not limited to, 1,2-bis(di-tert-butylphosphinomethyl)benzene, (±)-2,2'-Bis(diphenylphosphino)-1,1'-binaphthalene, Bis(2-(bis(diethylamino)phosphino)phenyl) ether, 1,1'-Bis[bis(dimethylamino)phosphino]ferrocene, 1,2-Bis(dichlorophosphino)ethane, 1,3-Bis(dicyclohexylphosphino)propane, 2-(Dicyclohexylphosphino)benzenesulfonic acid, 9,9-Dimethyl-4,5-bis(di-tert-butylphosphino)xanthene, 6,6'-[(3,3'-Di-tert-butyl-5,5'-dimethoxy-1,1'-biphenyl-2,2'-diyl)bis(oxy)]bis(dibenzo[d,f][1,3,2]dioxaphosphepin).

Suitable solid silica support acid include, but are not limited to, solid silica supported sulfonic acid, such as SiliaBond®, available from SiliCycle Inc. of Quebec, Canada.

The α, ω-nonadecanediester formed in the reaction is crystallized. The crystallized α, ω-nonadecanediester is then filtered from the reaction mixture. The crystallized α, ω-nonadecanediester is dissolved in a first solvent to form a first solution. The Group VIIIB element and the solid silica support acid are filtered from the first solution. Although not wishing to be bound by theory, it is believed that a majority of the Group VIIIB element adsorbs to the solid silica support. Some of the Group VIIIB element may be carried with the ligand. The first solvent is removed from the first solution to provide a recrystallized α, ω-nonadecanediester.

In some embodiments, the Group VIIIB element and the solid silica support acid are recycled to the reactor.

In some embodiments, the filtrate is mixed with a second solvent to form a second solution and an insoluble ligand portion. The insoluble ligand portion is then recycled to the reactor.

The reaction takes place at a temperature in the range of range of about 60° C. to about 100° C., and a pressure of about 5.5 MPa (g) to about 8.3 MPa (g).

It has been shown that a resin acid catalyst can be used in the process in order to simplify final purification because methanesulfonic acid could be difficult to remove. Also, the process can be applied to any mixture of free fatty acids. The procedure has been applied successfully to the triglyceride of high oleic soybean oil resulting in similar yield and purity of saturated $C_{19}$ dimethyl ester. The difference is in the production of glycerol and trace impurities of glycerides. However, the same purification scheme used with the alkyl ester starting material was applied to the triglycerides.

The yield of saturated $C_{19}$ dimethyl ester is dependent upon the oleic content of the starting feedstock. When the process was run using 22.24 g of normal soybean oil, only 5.97 g of 90.4 mol % (and 90% saturated) $C_{19}$ dimethyl ester was obtained, compared with 15 g of $C_{19}$ dimethyl ester when high oleic soybean oil was used. Consequently, a second recrystallization step was needed when normal oleic soybean oil was used as the starting material to obtain the same purity as when high oleic soybean oil was used as the starting material with a single recrystallization step.

In some cases, it is desirable to minimize the amount of co-products formed in order to obtain an increased yield of saturated $C_{19}$ diesters. One way to minimize the co-products is to use a feedstock with a higher oleic content than normal soybean oil, e.g., greater than 40 wt %, or greater than 45 wt %, or greater than 50 wt %, or greater than about 55 wt %, or greater than about 60 wt %, or greater than about 65 wt %, or greater than about 70 wt %, or greater than about 75 wt %, or greater than about 80 wt %, or greater than about 85 wt %, or greater than about 90 wt %.

With normal soybean oil, unsaturated diesters are present in the product in larger amounts due to the increased percentages of polyunsaturated fatty acids, such as linoleic and linolenic, in the normal soybean oil feedstock. Saturated monoesters are also present. The unsaturated diester products do not readily crystallize and therefore lower the yield and purity of the saturated diester product. Unsaturated diesters could be useful in some processes if purification was carried out to remove the monoester impurity. This product stream could also be reduced under mild hydrogenation conditions and then crystallized to give saturated $C_{19}$ dimethyl ester. However, this adds extra steps as compared to starting with soybean oil (or another oil) with a higher oleic content.

The process provides a number of advantages over known processes. The use of high oleic triglyceride oils or high oleic free fatty acid alkyl esters reduces the amount of non-crystalline products resulting in an increased crystallization yield. In addition, the use of a solid silica support acid eliminates the need for neutralization of the acid after the reaction. Moreover, the solid silica support acid can simply be filtered from the product solution and recycled to the reactor. In some embodiments, the Group VIIIB metal catalyst accumulates on the surface of the solid silica support acid and can be recycled along with the solid silica support acid. The process also allows the ligand to be isolated and recycled.

Other aspects of the invention include derivatives of α, ω-nonadecanediesters, and processes of making those derivatives.

The dicarboxylic acids typically used in the plastic industry have a chain length below 12 carbon atoms. The present invention allows the production and use of novel derivatives of $C_{19}$ dicarboxylic acid.

For example, the α, ω-nonadecanediester can be hydrolyzed to a α, ω-nonadecanedicarboxylic acid.

In another embodiment, the derivative can be an α, ω-nonadecane di-metal salt. The α, ω-nonadecane di-metal salt is soluble in water, and it gels at a concentration of about 10 wt %. For example, if a 10 wt % di-sodium nonadecane salt is heated in water to about 70° C. to about 80° C. until it is clear, it will form a gel when it is cooled to room temperature. In contrast, $C_6$ to $C_9$ diacids gel at a concentration of about 30 wt % to about 40 wt %. Gelation at lower concentrations may lower the cost of the product and may improve the incorporation of the di-metal salt into formulations. In addition, the structure is unique because there is a mixture of crystalline and amorphous regions.

The α, ω-nonadecane di-metal salt can be used as an encapsulant for pesticides, percarbonates, sunscreen additives, fragrances, and as an additive to moderate crystal nucleation.

In some embodiments, the α, ω-nonadecane di-metal salt can be formed by reacting an α, ω-nonadecane diester with a metallic or ammonium base in the presence of a solvent. In some embodiments, the metallic base can be a hydroxide, oxide, or oxyhalide of an alkali metal, an alkaline earth metal, a transition metal. The ammonium base is a base derived from ammonia (e.g., ammonium hydroxide, triethyl amine, triethanol amine and the like). As used herein, the term "di-metal salt" includes salts formed from metal bases as well as salts formed from ammonium bases.

In some embodiments, the solvent can be an alcohol. Suitable alcohols include, but are not limited to, alcohols containing 1 to 6 carbon atoms.

In some embodiments, the reaction can take place at a temperature in a range of about 60° C. to about 200° C.

Another example of a derivative is an α, ω-nonadecane di-poly alkoxy alcohol. The α, ω-nonadecane di-poly alkoxy alcohol has a triblock structure: a poly alkoxy alcohol portion on both sides of the nonadecane.

The α, ω-nonadecane di-poly alkoxy alcohol forms a micelle at about the same concentration as a commercially available block co-polymer with a similar theoretical HLB (Hydrophilic-Lipophilic Balance) value. For example, α, ω-nonadecane di-poly alkoxy alcohol (Example 8) had a CMC (Critical Micelle Concentration) of 0.01 (g/100 ml), while a commercially available petroleum based block surfactant, Pluronic L-64 (available from BASF), had a CMC of 0.01 (g/100 ml).

The α, ω-nonadecane di-poly alkoxy alcohol can be used as a surfactant for coatings and cosmetic formulations.

In some embodiments, the α, ω-nonadecane di-poly alkoxy alcohol can be formed by reacting the α, ω-nonadecane diester with a poly alkoxy alcohol in the presence of a catalyst. The poly alkoxy alcohol can include one or more hydroxyl groups. In some embodiments, the poly alkoxy alcohol can be a poly(alkylene glycol), including derivatives of poly(alkylene glycol) such as mono-methyl ethers of poly(alkylene glycol). In some embodiments, the poly alkoxy alcohol comprises a poly(ethylene glycol) having a number average molecular weight (MW) in a range of about 200 to about 20,000, or about 200 to about 15,000, or about 200 to about 10,000, or about 200 to about 5000, or about 200 to about 4000, or about 200 to about 3000, or about 200 to about 2000, or about 300 to about 2000.

In some embodiments, the reaction can take place at a temperature in a range of about 60° C. to about 200° C., or about 90° C. to about 150° C., and a pressure of about 101 kPa (about 760 Torr) or less.

In some embodiments, the catalyst includes, but is not limited to, organo tin catalysts. Suitable organo tin catalysts include, but are not limited to, organo tin halides, organo tin oxides, and thiocyanate compounds, like Otera's catalysts. Examples of catalysts include, but are not limited to, dibutyl tin oxide and tin (II) 2-ethylhexanoate. Other catalysts can also be used, including but not limited to, boron trifluoride, potassium methoxide, and potassium t-butoxide.

Another derivative is an α, ω-nonadecane di-poly oxepan-2-one. This will also have a triblock structure with the poly oxepan-2-one portion on both sides of the nonadecane. It might be used as a biodegradable polymer for encapsulating drugs, for example.

In some embodiments, the α, ω-nonadecane di-poly oxepan-2-one can be formed by reacting the α, ω-nonadecanediester with a caprolactone polyol in the presence of a catalyst and/or a solvent. Any suitable transesterification catalyst could be used. In some embodiments, the catalyst comprises dibutyl tin oxide or tin (II) 2-ethylhexanoate. Suitable solvents include, but are not limited to, toluene, hexane, tetrahydrofuran (THF), butyl acetate, and methyl ethyl ketone. In some embodiments, the reaction can take place at a temperature in a range of about 60° C. to about 200° C., or about 90° C. to about 150° C., and a pressure of about 101 kPa (about 760 Torr) or less.

Yet another derivative is an α, ω-nonadecane di-benzimidizole. The α, ω-nonadecane di-benzimidizole might be used as a biocide or fungicide.

In some embodiments, the α, ω-nonadecane di-benzimidizole can be formed by reacting the α, ω-nonadecanediester with benzimidizole in the presence of a catalyst and solvent. In some embodiments, the solvent comprises polar aprotic solvents including, but not limited to, N-methyl-2-pyrrolidone (NMP), dimethyl acetamide (DMAC), dimethyl formamide (DMF), and sulfolane, toluene, tetrahydrofuran (THF), hexane, esters such as butyl acetate and cellosolve acetate, alcohols such as n-butanol and t-butanol, and ketones, such as methyl ethyl ketone (MEK) and methyl isobutyl ketone (MIBK). In some embodiments, the catalyst comprises Brønsted acids, including but not limited to, phosphoric acid, polyphosphoric acid, p-toluene sulfonic acid, and sulfuric acid, and mixtures thereof. In some embodiments, reaction conditions can take place at a temperature in a range of about 120° C. to about 240° C., and a pressure of about 0.01 psig to about 500 psig.

Still another derivative is an α, ω-nonadecane alt-(amine) where the alt-(amine) is derived from piperazine, 1,4-diamino cyclohexane, isophorone diamine, and dicyclohexyl methane diamine. The α, ω-nonadecane alt-(amine) could be used in automotive or industrial applications, such as plasticizers, coatings, films, adhesives, resins, and plastics.

In some embodiments, the α, ω-nonadecane dialkylester is reacted with an amine selected from piperazine, 1,4-diamino cyclohexane, isophorone diamine, and dicyclohexyl methane diamine, without any solvent, in the presence of a transesterification catalyst at a temperature in a range of about 60° C. to about 280° C., or about 90° C. to about 270° C., and a pressure of about 0.01 psig to about 1000 psig to form polyamides (if a primary amine reacted, e.g., 1,4-diamino cyclohexane, and dicyclohexyl methane diamine), polyimides (if a secondary amine is reacted, e.g., piperazine), or poly(amide-imides) (if a mixture of primary and secondary amines is reacted, e.g., isophorone diamine) with number average molecular weight ranges between 2000 and 100,000. Suitable transesterification catalysts include, but are not limited to, dibutyl tin oxide or tin (II) 2-ethylhexanoate.

Another aspect of the invention involves a method of making a linear α, ω-nonadecanediester or diester derivative. In one embodiment, the method comprises: contacting a feed comprising a vegetable oil, a free fatty acid alkyl ester mixture, or an animal fat wherein at least about 50% of the fatty acid radicals or free fatty acid groups are oleic acid with an alcohol in the presence of carbon monoxide, a catalyst comprising a Group VIIIB element and a phosphorus containing ligand, and a solid silica support acid in a reactor to form a reaction mixture comprising the α, ω-nonadecanediester, the catalyst, and the solid support acid; crystallizing the α, ω-nonadecanediester; filtering the crystallized α, ω-nonadecanediester from the reaction mixture to form a filtrate; dissolving the crystallized α, ω-nonadecanediester in a first solvent to form a first solution; filtering the Group VIIIB element and the solid silica support acid from the first solution; and removing the first solvent from the first solution to provide a recrystallized α, ω-nonadecanediester.

In some embodiments, the method further comprises: recycling the Group VIIIB element and the solid silica support acid to the reactor.

In some embodiments, the first solvent comprises chlorinated solvents, such as dichloromethane, alkanes, alkenes, ketones, and aromatics. In some embodiments, the alkanes, alkenes, ketones, and aromatics are used at temperatures of about 80° C. or more.

In some embodiments, the method further comprises: mixing the filtrate with a second solvent, such as hexane, to form a second solution and an insoluble ligand portion; and recycling the insoluble ligand portion to the reactor. The second solvent can be the same as, or different from, the first solvent. Suitable second solvents include, but are not limited to, chlorinated solvents, alkanes, alkenes, ketones, and aromatics.

In some embodiments, the solid silica support acid comprises a solid silica supported sulfonic acid.

In some embodiments, the Group VIIIB comprises palladium.

In some embodiments, the phosphorus containing ligand comprises 1,2-bis(di-tert-butylphosphinomethyl)benzene.

In some embodiments, the alcohol includes, but is not limited to, methanol, ethanol, propanol, and isopropanol.

In some embodiments, the reaction conditions include at least one of: a temperature in a range of about 60° C. to about 180° C., and a pressure of about 0.01 psig to about 1200 psig.

In some embodiments, the feed comprises high oleic soybean oil, high oleic canola oil, high oleic safflower oil, high oleic olive oil, mid-oleic soybean oil, carinata oil, alkyl esters of high oleic soybean oil, alkyl esters of high oleic canola oil, alkyl esters of high oleic safflower oil, alkyl esters of high oleic olive oil, alkyl esters of mid-oleic soybean oil, alkyl esters of carinata oil, or combinations thereof.

In some embodiments, at least about 70% of the fatty acid radicals or free fatty acid groups are oleic acid.

In some embodiments, the method further comprises: hydrolyzing the α, ω-nonadecanediester to a α, ω-nonadecanedicarboxylic acid.

In some embodiments, the method further comprises: reacting the α, ω-nonadecanediester with a metallic base or an ammonium base in the presence of a solvent to form an α, ω-nonadecane di-metal salt.

In some embodiments, the method further comprises: reacting the α, ω-nonadecanediester with a poly alkoxy diol in the presence of a catalyst to form an α, ω-nonadecane di-poly alkoxy diol.

In some embodiments, the method further comprises: reacting the α, ω-nonadecanediester with a caprolactone polyol in the presence of a catalyst to form an α, ω-nonadecane di-poly oxepan-2-one.

In some embodiments, the method further comprises: reacting the α, ω-nonadecanediester with benzimidizole in the presence of a catalyst to form an α, ω-nonadecane di-benzimidizole.

In some embodiments, the method further comprises: reacting the α, ω-nonadecanediester with an amine selected from piperazine, 1,4-diamino cyclohexane, isophorone diamine, and dicyclohexyl methane diamine in the presence of a catalyst to form an α, ω-nonadecane alt-(amine) wherein the alt-(amine) is derived from piperazine, 1,4-diamino cyclohexane, isophorone diamine, or dicyclohexyl methane diamine.

All possible combinations of features and embodiments are contemplated.

EXAMPLES

The reactions were performed in autoclaves under carbon monoxide pressure. The starting materials included high oleic soybean oil, normal saturated soybean oil, or the methyl esters thereof. All materials were measured under atmospheric conditions. The following is a description of the general reaction with respect to high oleic soybean oil methyl esters.

Example 1

43.37 g of high oleic soybean oil methyl esters was charged into an autoclave with 0.34 g palladium (II) chloride ($PdCl_2$), 3.42 g 1,2-bis(Di-tert-butylphosphinomethyl)benzene (DtBpx), 1.04 g methanesulfonic acid, and 196 mL methanol. The reactor was pressurized with 1030 psi carbon monoxide and heated to 80° C. for 24 hours. The resulting mixture was transferred to a jar, and the reactor was rinsed with 200 mL hot methanol which was also placed into the jar. The material was heated to homogenize it and then placed into freezer at −20° C. The mixture was then filtered through a coarse fritted filter to obtain a crystalline diester product. The solid product was dissolved into dichloromethane and filtered to remove 0.12 g of black particulate (Pd catalyst). The dichloromethane was removed by vacuum distillation. The resulting solid was dissolved into 200 mL hot hexane, decanted from 0.83 g insoluble material, and placed into a freezer. The cold hexane with crystalline product was filtered through a coarse fritted filter and washed twice with 50 mL cold hexane. The solid white flakes were placed into a vacuum oven overnight to remove trace hexane. 31.30 g of 99 mol % saturated $C_{19}$ dimethyl ester was obtained. The total reaction mass balance was 98.8%.

Example 2

The reaction was next run using resin acid in place of the methanesulfonic acid. 22.12 g of high oleic soybean oil methyl esters was charged into an autoclave with 0.17 g $PdCl_2$, 1.76 g DtBpx, 3.5 mL washed Amberlite™ IR-120 resin (available from Dow Chemical Co.), and 110 mL methanol. The reactor was pressurized with 1105 psig (7.6 MPa (g)) carbon monoxide and heated to 90° C. for 24 hours. The resulting mixture was transferred to a jar and placed into the freezer at −20° C. The crystalline diester was then dissolved into hot hexane and filtered through a Whatman number 1 paper filter to remove the resin and catalyst. The homogeneous hot hexane was placed back into the freezer. Once crystallized, the mixture was filtered through a coarse fritted filter and rinsed with cold hexane. The solid was placed into the vacuum oven to remove hexane residual. 15.20 g of 96.8 mol % saturated $C_{19}$ dimethyl ester was obtained.

Example 3

The reaction was run using another resin acid. 97.38 g of high oleic soybean oil methyl esters was charged into an autoclave with 0.72 g $PdCl_2$, 1.93 g DtBpx, 9.65 g washed Siliabond® Propylsulfonic acid (available from SiliCycle® Inc.), and 280 mL methanol. The reactor was pressurized with 1050 psig (7.2 MPa (g)) carbon monoxide and heated to 80° C. for 24 hours. The resulting mixture was transferred to a jar and placed into the freezer at −20° C. The mixture was then filtered through a coarse fritted filter and the filter cake was rinsed twice with 100 mL cold methanol. The filter cake was then washed with 200 mL boiling methanol and filtered followed by 100 mL more boiling methanol twice. The filtrate was homogenized with heat and recrystallized. The resulting mixture was filtered and rinsed twice with 100 mL cold methanol. The resulting solid was placed into the vacuum oven to remove methanol residual. 74.33 g of 96.2 mol % saturated $C_{19}$ dimethyl ester was obtained.

Example 4

The resin and catalyst portions of the previous reaction were recycled for a reaction of 22.10 g high oleic soybean oil methyl esters with 1020 psig (7.0 MPa (g)) carbon monoxide and 110 mL methanol in an autoclave. The reaction was run at 90° C. for 24 hours. The same procedure was followed for work-up. 10.80 g of 97.1 mol % saturated $C_{19}$ dimethyl ester was obtained.

Example 5: Di-Sodium Salt of $C_{19}$ Diester 1.2736 g of sodium hydroxide was dissolved in 1.2200 g of distilled water and 61.1 g of methanol. This was charged with 10.0001 g of $C_{19}$ dimethyl ester into a round bottom flask with a water cooled condenser placed in a temperature controlled mineral oil bath. The mixture was heated to 60° C. and allowed to mix overnight. The excess base was neutralized to 7.5 pH with HCl. The product was precipitated in isopropyl alcohol (IPA), and the solids were dried.

Example 6: Di-Calcium Salt of $C_{19}$ Diester 1.78 g of calcium oxide was dissolved in 1.2200 g of distilled water and 65 g of methanol. This was charged with 10.0 g of $C_{19}$ dimethyl ester into a round bottom flask with a water cooled condenser placed in a temperature controlled mineral oil bath. The mixture was heated to 60° C. and allowed to mix overnight. The excess base was neutralized to 7.5 pH with HCl. The product was precipitated in IPA, and the solids were dried.

Example 7: Di-Zirconium Salt of $C_{19}$ Diester 5.65 g of zirconium oxychloride was dissolved in 1.50 g of distilled water and 60 g of methanol. This was charged with 10.00 g of $C_{19}$ dimethyl ester into a round bottom flask with a water cooled condenser placed in a temperature controlled mineral oil bath. The mixture was heated to 60° C. and allowed to mix overnight. The excess base was neutralized to 7.5 pH with HCl. The product was precipitated in IPA, and the solids were dried.

Example 8: Poly Alkoxy Derivative of $C_{19}$ Diester 9.9997 g $C_{19}$ dimethyl ester, 36.6719 g of 550 MW poly(ethylene glycol) methyl ether, and 0.2373 g dibutyl tin oxide were charged in a 50 mL roundbottom flask fitted with an overhead stirrer, vacuum outlet, with a temperature controlled mineral oil bath. After charging, the oil bath was heated to 120° C., and the mixture was allowed to react for 3 hours at temperature under full vacuum.

Example 9: Poly Alkoxy Derivative of $C_{19}$ Diester 1.2765 g $C_{19}$ dimethyl ester, 16.9651 g of 2000 MW poly(ethylene glycol) methyl ether, and 0.0560 g dibutyl tin oxide were charged in a 50 mL roundbottom flask fitted with an overhead stirrer, vacuum outlet, with a temperature controlled mineral oil bath. After charging, the oil bath was heated to 120° C., and the mixture was allowed to react for 3 hours at temperature under full vacuum.

Example 10: Poly Alkoxy Derivative of $C_{18}$ Diester 10.0790 g $C_{19}$ dimethyl ester (Emerox 118 diacid available from Emery Oleochemicals and converted to a diester), 38.9148 g of 550 MW poly(ethylene glycol) methyl ether, and 0.263 g dibutyl tin oxide were charged in a 50 mL roundbottom flask fitted with an overhead stirrer, vacuum outlet, with a temperature controlled mineral oil bath. After charging, the oil bath was heated to 120° C., and the mixture was allowed to react for 3 hours at temperature under full vacuum.

Example 11: Poly Alkoxy Derivative of $C_{19}$ Diester 3.015 g $C_{19}$ dimethyl ester, 39.99 g of 550 MW poly(ethylene glycol), and 0.1281 g dibutyl tin oxide were charged in a 50 mL roundbottom flask fitted with an overhead stirrer, vacuum outlet, with a temperature controlled mineral oil bath. After charging, the oil bath was heated to 120° C., and the mixture was allowed to react for 3.5 hours at temperature under full vacuum.

Example 12: Poly Oxepan-2-One Derivative of $C_{19}$ Diester 14.8 g $C_{19}$ dimethyl ester, 24.9 g caprolactone polyol (CAPA™ 2054, available from Perstorp Group of Sweden), and 0.0558 g dibutyl tin oxide were charged into a 250 mL roundbottom flask fitted with a vacuum outlet with dry ice trap, an overhead stirrer and heating mantle with a temperature controller, and thermocouple network. The contents were heated to 80° C. for 4 hours, then heated up to 120° C. overnight while pulling full vacuum. The molten polymer was poured into a jar while still a warm liquid. It hardened while cooling into a grey solid.

Example 13: Poly Oxepan-2-One Derivative of $C_{19}$ Diester 13.6 g $C_{19}$ dimethyl ester, 22.9 g caprolactone polyol (CAPA™ 2054, available from Perstorp Group of Sweden), and 0.1817 g tin (II) 2-ethylhexanoate (Aldrich) were charged in a 250 mL roundbottom flask fitted with a vacuum outlet with dry ice trap, an overhead stirrer and heating mantle with a temperature controller, and thermocouple network. The contents were heated to 140° C. for 1 hour, then heated to 180° C. overnight while pulling full vacuum for approximately 20 hours. The molten polymer was poured into a jar while still a warm liquid at about 80° C. It hardened while cooling into a brown waxy solid.

Example 14: Benzimidizole Derivative 1.99 g $C_{19}$ diacid (disodium derivative), 1.15 g 1,2-phenylenediamine, 125 mL dimethylacetamide (DMAc), 20 mL n-butanol, and 25 mL toluene were charged to a 250 ml flask equipped with a thermocouple, a dry air inlet, a mechanical stir, and a dean-stark trap with a water cooled condenser and a vigreux column. The mixture was stirred at room temperature until the disodium salt dissolved. Once the sodium salt was dissolved, 4.96 g ortho phosphoric acid was charged, and the flask was heated until the toluene azeotrope formed to remove the water. Once all of the water was removed, the material was slowly heated to 150° C. The heating was slow enough to control the reflux at an acceptable rate (no more than 3 mL of solvent collected in the dean stark trap for every minute). It was held at reflux for 3 hours. After the 3 hours, the trap was drained and the toluene and the butanol were collected. The temperature was maintained below 162° C. to prevent removal of the DMAC. Once all of the toluene/butanol was removed, the mixture was slowly cooled to room temperature. When the reaction reached room temperature, the contents was charged to distilled water to precipitate the product. The product obtained was centrifuged and the wet product was dried in an air circulatory over at 120° C. for 12 hours.

Example 15: Piperazine Derivative 40.4 g $C_{19}$ dimethyl ester, 10.9 g piperazine, and 0.8 g dibutyl tin oxide were charged in a roundbottom flask fitted with an overhead stirrer, a vacuum outlet, and a thermocouple-heating mantle and temperature controller network. The mixture was heated to 120° C. under vacuum while mixing the piperazine derivative of $C_{19}$ diacid.

As used herein, the term about means within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of making a linear α, ω-nonadecanediester derivative comprising:
   reacting a linear α, ω-nonadecanediester or a linear α, ω-nonadecanedicarboxylic acid with a reactant optionally in the presence of at least one of a solvent and a catalyst to form the α, ω-nonadecanediester derivative; wherein the reactant is a poly alkoxy alcohol, and the α, ω-nonadecanediester derivative is an α, ω-nonadecane di-poly alkoxy alcohol, and wherein the poly alkoxy alcohol comprises a poly(ethylene glycol) having a MW in a range of 300±1% to about 20,000; or wherein the reactant is a caprolactone polyol and the α, ω-nonadecanediester derivative is an α, ω-nonadecane di-poly oxepan-2-one; or wherein the reactant is benzimidizole, and wherein the α, ω-nonadecanediester derivative is an α, ω-nonadecane di-benzimidizole; or wherein the reactant is an amine selected from piperazine, 1,4-diamino cyclohexane, isophorone diamine, and dicyclohexyl methane diamine, and wherein the α, ω-nonadecanediester derivative is an α, ω-nonadecane alt-(amine) wherein the alt-(amine) is derived from piperazine, 1,4-diamino cyclohexane, isophorone diamine, or dicyclohexyl methane diamine.

2. The method of claim 1 wherein the reactant is the poly alkoxy alcohol, and the α, ω-nonadecanediester derivative is the α, ω-nonadecane di-poly alkoxy alcohol; and wherein the α, ω-nonadecanediester or the α, ω-nonadecanedicarboxylic acid is reacted in the presence of the catalyst.

3. The method of claim 2 wherein the catalyst comprises an organo tin catalyst.

4. The method of claim 2 wherein reaction conditions comprise one or more of: a temperature in a range of about 60° C. to about 200° C., or a pressure of about 101 kPa or less.

5. The method of claim 1 wherein the reactant is the caprolactone polyol and the α, ω-nonadecanediester derivative is the α, ω-nonadecane di-poly oxepan-2-one; and wherein the α, ω-nonadecanediester or the α, ω-nonadecanedicarboxylic acid is reacted in the presence of the catalyst.

6. The method of claim 5 wherein the catalyst comprises an organo tin catalyst.

7. The method of claim 5 wherein reaction conditions comprise one or more of: a temperature in a range of about 60° C. to about 200° C., or a pressure of about 101 kPa or less.

8. The method of claim 1 wherein the reactant is benzimidizole, and wherein the α, ω-nonadecanediester derivative is the α, ω-nonadecane di-benzimidizole; and wherein the α, ω-nonadecanediester or the α, ω-nonadecanedicarboxylic acid is reacted in the presence of the solvent and the catalyst.

9. The method of claim 8 wherein the solvent comprises N-methyl-2-pyrrolidone, dimethyl acetamide, dimethyl formamide, sulfolane, toluene, tetrahydrofuran, hexane, butyl acetate, cellosolve acetate, n-butanol, t-butanol, methyl ethyl ketone, and methyl isobutyl ketone.

10. The method of claim 8 where the catalyst comprises sulfuric acid, p-toluene sulfonic acid, phosphoric acid, polyphosphoric acid, and mixtures thereof.

11. The method of claim 8 wherein reaction conditions comprise one or more of: a temperature in a range of about 120° C. to about 220° C., or a pressure of about 0.01 psig to about 500 psig.

12. The method of claim 1 wherein the reactant is the amine selected from piperazine, 1,4-diamino cyclohexane, isophorone diamine, and dicyclohexyl methane diamine, and wherein the α, ω-nonadecanediester derivative is the α, ω-nonadecane alt-(amine) wherein the alt-(amine) is derived from piperazine 1,4-diamino cyclohexane, isophorone diamine, or dicyclohexyl methane diamine; and wherein the α, ω-nonadecanediester or the α, ω-nonadecanedicarboxylic acid is reacted in the presence of the catalyst.

13. The method of claim 12 wherein the catalyst comprises an organo tin catalyst.

14. The method of claim 12 wherein reaction conditions comprise one or more of: a temperature in a range of about 60° C. to about 280° C., or a pressure of about 0.01 psig to about 1000 psig.

15. An α, ω-nonadecanediester derivative comprising an α, ω-nonadecane di-poly alkoxy diol, an α, ω-nonadecane di-poly oxepan-2-one, an α, ω-nonadecane di-benzimidizole, or an α, ω-nonadecane alt-(amine) wherein the alt-(amine) is derived from piperazine, 1,4-diamino cyclohexane, isophorone diamine, or dicyclohexyl methane diamine.

* * * * *